(12) United States Patent
Hildebrandt

(10) Patent No.: US 9,032,551 B2
(45) Date of Patent: May 19, 2015

(54) COMPRESSION STOCKING APPLICATOR

(75) Inventor: Barry George Hildebrandt, Gumlu (AU)

(73) Assignee: EZY-AS ABC PTY LTD, Croydon, Victoria (AU)

(*) Notice: Subject to any disclaimer, the term of this patent is extended or adjusted under 35 U.S.C. 154(b) by 1137 days.

(21) Appl. No.: 12/373,473

(22) PCT Filed: Jul. 2, 2007

(86) PCT No.: PCT/AU2007/000917
§ 371 (c)(1),
(2), (4) Date: Jan. 12, 2009

(87) PCT Pub. No.: WO2008/006142
PCT Pub. Date: Jan. 17, 2008

(65) Prior Publication Data
US 2009/0242593 A1    Oct. 1, 2009

(30) Foreign Application Priority Data
Jul. 14, 2006  (AU) .............................. 2006203009

(51) Int. Cl.
*A47G 25/80* (2006.01)
*A47G 25/90* (2006.01)
*A61F 13/04* (2006.01)
*A61F 13/08* (2006.01)

(52) U.S. Cl.
CPC ............ *A47G 25/905* (2013.01); *A47G 25/908* (2013.01); *A61F 13/041* (2013.01); *A61F 13/085* (2013.01)

(58) Field of Classification Search
USPC .................................................. 223/111–112
See application file for complete search history.

(56) References Cited

U.S. PATENT DOCUMENTS

| 1,861,385 | A | * | 5/1932 | Gentil | 223/111 |
| 4,789,087 | A | * | 12/1988 | Doorenbos | 223/111 |
| 5,630,534 | A | * | 5/1997 | Maier et al. | 223/112 |
| 5,826,761 | A |   | 10/1998 | Basaj |  |
| 5,909,831 | A | * | 6/1999 | Griffin | 223/112 |

(Continued)

FOREIGN PATENT DOCUMENTS

| AU | 2006100070 A4 | 2/2006 |
| EP | 1576910 A1 | 9/2005 |

(Continued)

OTHER PUBLICATIONS

Melhuish, David, International Search Report and Written Opinion, PCT/US2007/000917, Australian Patent Office, Jul. 23, 2007.
Beins, Ulrika, Supplementary European Search Report, EP 07 71 9154, Jul. 12, 2013, European Patent Office.

*Primary Examiner* — Shaun R Hurley
*Assistant Examiner* — Andrew W Sutton
(74) *Attorney, Agent, or Firm* — Joseph R. Baker, Jr.; Gavrilovich, Dodd & Lindsey LLP

(57) ABSTRACT

The disclosure provides a medical compression stocking applicator having an elongate member which has a pair of opposed sidewalls and an interconnecting wall and therefore may be substantially U-shaped in cross-section and is open at each end. The elongate member also includes a heel opening between the ends of the elongate member. The heel opening extends entirely through the elongate member, and is adapted to support a person's heel during application of a stocking.

20 Claims, 14 Drawing Sheets

(56) References Cited

U.S. PATENT DOCUMENTS 7,070,074 B2    7/2006    Landsbuger et al.
2008/0185407 A1*    8/2008    Wilkens ..................... 223/112

FOREIGN PATENT DOCUMENTS

| EP | 1 674 005 A1 | 6/2006 |
|---|---|---|
| WO | 2007085061 A1 | 8/2007 |

\* cited by examiner

16

COMPRESSION STOCKING APPLICATOR

CROSS REFERENCE TO RELATED APPLICATIONS

The present application is a National Stage Application filed under Section 371 and claims priority to International Application No. PCT/AU2007/000917, filed Jul. 2, 2007, which application claims priority to Australian Application No. 2006203009, filed Jul. 14, 2006, the disclosures of which are incorporated herein by reference.

FIELD OF THE INVENTION

This invention is directed to a small and easily used device to allow a person to put on a compression stocking. Although the invention will be described with reference to a compression stocking, the device can also be used on other types of stockings, socks etc where there is an advantage in using the device. The device can also be used to fit a compression bandage to a person's arm or somewhere else.

BACKGROUND ART

A compression stocking generally comprises an elastic sock which can be fitted to a person to provide compression. The stockings are generally used to improve circulation. Compression stockings are well known in the art and are sometimes called elastic stockings, medical stockings, compression socks, compression/tubular bandages and the like.

These stockings are used for burns victims, on patients before having operations, to prevent deep vein thrombosis, for patients with vascular diseases, for treatment of topical ulcers, for varicose veins, for the prevention of strokes, for patients recovering from knee replacement surgery, for aged care nurses and nursing homes, for patients who are bedridden, for the protection of wounds, for patients with a fused ankle joints, for disabled and wheelchair-bound patients, for sports injuries and the like.

The stockings may have an open toe or a closed toe.

The stockings are typically made of relatively fine elastic material and it is this property that also makes the stockings difficult to apply as it is necessary to keep the stocking open and to fit the stocking about the person's foot and leg. Thus, many compression stockings do not simply slide onto a person's foot and rather need to be manipulated onto the person's foot/leg/arm. For this reason, many types of applicators are known to assist in the donning of a stocking.

The present invention is directed to a unique type of applicator which is easy to operate, quick to operate, is a user-friendly, can be used both on arms and legs, and has various other advantages which will be described hereinafter.

As mentioned previously, there are many types of applicators which are known. For instance, it is known to provide an applicator which comprises a metal ring. The open end of the stocking can be stretched about the ring to make it easier to don the stocking over a person's foot and calf area. However, it is found that the ring has some disadvantages. Firstly, once the stocking has been fitted, the ring needs to be removed by sliding it back over the person's foot, and some people may find it difficult to do this and particularly to pick up the ring afterwards. Also, the ring does not provide a very easy application of the compression stocking over the entire limb (that is the foot, ankle and calf).

Another type of applicator comprises a more complicated wire structure which is inserted into the stocking.

Most of these "wire" type applicators suffer from the disadvantage that they are designed to be placed on the floor and the patient is required to lower their foot into the device. Therefore, this type of applicator can generally not be used if the patient is sitting, has one leg crossed over the other leg, or lying down in bed.

Some type of applicators comprise a rigid or substantially rigid tube which may have some advantages over the simple ring, but suffer from the same disadvantage of needing to be removed back over the foot and not being entirely satisfactory in fitting the stocking.

Quite complicated mechanical stocking applicators are also known but these applicators are expensive to manufacture, difficult to use, and difficult, if not impossible, to transport with the person.

It is also known to provide a modified type of shoehorn to assist in the fitting of a medical stocking.

The disadvantage with removal of the applicator after use, but still providing a simple applicator, has been partially overcome by providing an applicator which comprises a U-shaped channel about which the stocking can be fitted. The channel, after use, allows the applicator to be removed from the person's limb without needing to pass back over the person's foot.

A disadvantage with many applicators is also in the easy use of the applicator. That is, many applicators are not particularly suited to easily fit a stocking over the person's foot, past the person's heel, over the ankle and along the person's calf. It should be appreciated that many people find this particular maneuver extremely difficult. For instance, the applicator should allow a person to fit a stocking quite easily over and around the heel portion and ankle portion which requires an angle change in the applicator. It is found that it can be quite painful for many people to use a stocking applicator due to the need to twist the person's limb during application, or to bend or stretch etc during the application process.

A disadvantage with other applicators is that it is somewhat fiddly to fit the stocking to the applicator prior to applying the stocking to a person's limb. Sometimes, it is necessary to provide quite a large force or effort to fit the stocking to the applicator. As the stocking can be quite flimsy and also quite expensive, it is not satisfactory to have a system where the stocking can be torn. Therefore, in many situations, the stocking is loaded onto the applicator by somebody else such as the caretaker, the nurse, hospital staff, a family member etc.

Other types of applicators are suitable only for the lower limbs and are not particularly suited for upper limbs.

It will be clearly understood that, if a prior art publication is referred to herein, this reference does not constitute an admission that the publication forms part of the common general knowledge in the art in Australia or in any other country.

Throughout this specification, the term "comprising" and its grammatical equivalents shall be taken to have an inclusive meaning unless the context of use indicates otherwise.

OBJECT OF THE INVENTION

It is an object of the invention to provide a stocking applicator which may overcome at least some of the above-mentioned disadvantages or provide a useful or commercial choice.

In one form, the invention resides in a stocking applicator, the applicator comprising an elongate member which is substantially U-shaped and is open at each end, the elongate member comprising a heel opening between the ends of the elongate member, said heel opening extending entirely through the elongate member, the heel opening adapted to support a person's heel during application of a stocking.

Suitably, a raised surface is provided at least partially about at least one end of the applicator. The raised surface can function as a stocking stop and/or a grip enhancing surface.

Suitably, the applicator has a length of between 10-50 cm.

The applicator may be made from smooth material to facilitate application of the stocking. In one form, the applicator can be made of smooth plastic and PVC (polyvinyl chloride) may be an example of a smooth plastic. Of course, the applicator may be made of other smooth plastic materials or other smooth non-plastic materials such as fibreglass, wood, metal, glazed materials and the like.

Suitably, one end of the applicator is formed substantially flat (for instance square cut) and this end is preferably the "base" or "lower end" of the applicator in use.

Suitably, the other "upper" end of the applicator is angled downwardly.

The applicator is typically shaped such that it has a pair of opposed sides and an interconnecting portion. In practice, the applicator will typically comprise a unitary structure. The interconnecting portion may be rounded or may have another configuration.

It is envisaged that the opposed sides will be substantially parallel to each other although the sides may also converge or diverge relative to each other.

The heel opening is preferably positioned in the interconnecting portion of the elongate member.

If desired, more than one heel opening may be provided.

The heel opening may comprise an oval shape, a circular shape, or another shape which can function as a heel opening and also function to facilitate application of a stocking.

It is envisaged that the heel opening will have a length or diameter of between 20-100 mm and typically between 40-80 mm. It is envisaged that the heel opening will have a width of between 20-100 mm and typically between 20-60 mm.

If desired, the applicator may be provided with some form of "closure" to cover the heel opening when not required (for instance if the applicator is used on an upper limb) and where the closure can be removed. However, it is considered practical to simply have the heel opening open at all times.

The applicator may have any suitable length. It is considered that a suitable length will be between 10-50 cm, although there may be some circumstances where the applicator is larger or smaller than these dimensions (for instance for use on infants).

It is envisaged that the applicator will be relatively rigid during use. However, the applicator may have a degree of flex if desired.

It is envisaged that the applicator may be manufactured in such a manner that it can be "flat stacked" for storage and transportation and then "erected" for use. For instance, the applicator may be made in two or more removable parts which can be assembled prior to use. Alternatively, some form of hinge or flex arrangement may be provided.

In another form, the invention resides in an applicator substantially as described above together with a stocking fitted to the applicator.

In another form, the invention resides in a method of applying a stocking to a person's lower limb the method comprising providing an applicator which comprises a substantially U-shaped elongate body having a heel hole extending entirely through the elongate body intermediate the ends of the body, stretching an upper end of the stocking over one end of the applicator, pushing the stocking over the outside of the applicator towards the other end of the applicator until the heel portion of the stocking is adjacent the one end of the applicator, placing a person's heel in the heel portion of the stocking, pulling the applicator along the person's foot such that the person's heel enters into the heel hole of the applicator, and then moving the applicator up the person's calf area until such time as the stocking has been applied, and then removing the applicator from the person's leg.

In another form, the invention resides in a method of removing a stocking from a person's lower limb the method comprising placing an applicator which comprises a substantially U-shaped elongate body having a heel hole extending entirely through the elongate body intermediate the ends of the body against the limb, stretching an upper end of the stocking over one end of the applicator, pushing the stocking over the outside of the applicator towards the other end of the applicator, adjusting the position of the applicator to allow a person's heel to be placed in the heel hole, moving the applicator along the person's foot until such time as the stocking has been removed or the person is able to remove the foot from the stocking.

In another form, the invention resides in a stocking applicator comprising an elongate member which comprises a pair of opposed sidewalls and an interconnecting wall and therefore may be substantially U-shaped in cross-section and is open at each end, the elongate member having an opening in the interconnecting wall which is adapted to support part of a person's limb (for example a heel or elbow) during application of a stocking over the limb, wherein said opening extends entirely through the elongate member.

In some embodiments of the present invention, the applicator may further comprise means for assisting in the application of a stocking. These means may be of any suitable form, although in some preferred embodiments of the invention, the means may comprise one or more handles. The handles may be of any suitable form, such as, but not limited to, handles with rigid or flexible connectors interconnecting the handles and the applicator. The handles may be permanently or removably attached to the applicator and may be constructed from any suitable material, such as, but not limited to, plastic, metal, rubber and the like.

In some further embodiments of the invention, an inner surface of the elongate member may be provided with one or more raised portions. The raised portions may comprise any suitable form, although in some embodiments of the invention, the raised portions comprise one or more ribs. The ribs may be located at any point on the inner surface of the elongate member. In one embodiment of the present invention, the ribs are located on the inner surface of the interconnecting wall. In a preferred embodiment of the invention, the ribs are located adjacent the heel opening in the elongate member. The number and placement of these ribs serves to allow the thickness of the elongate member at the heel opening to be reduced while still retaining sufficient rigidity to load and apply a high compression stocking.

BRIEF DESCRIPTION OF THE DRAWINGS

Embodiments of the invention will be described with reference to the following drawings in which.

DETAILED DESCRIPTION OF THE INVENTION

Figure 1:
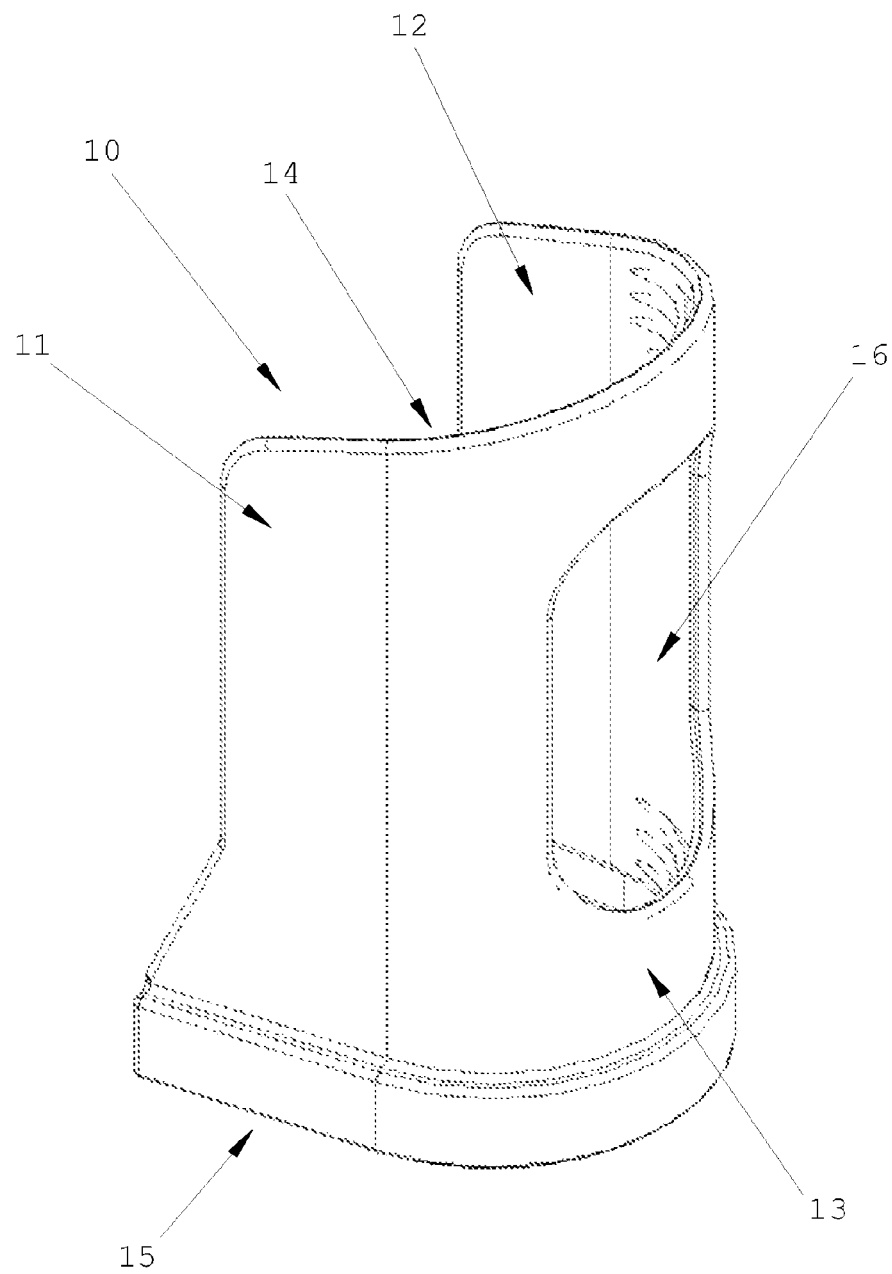
FIG. 1. Illustrates a stocking applicator according to an embodiment of the invention.
Figure 2:
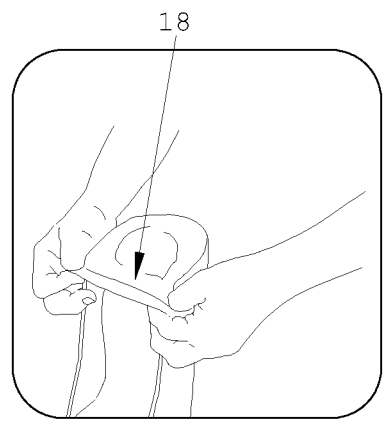
FIGS. 2-4. Illustrate progressively how a stocking is attached to the applicator.
Figure 3:
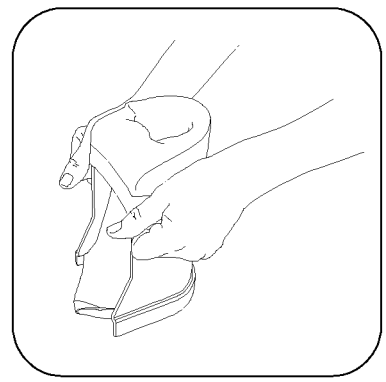
Figure 4:
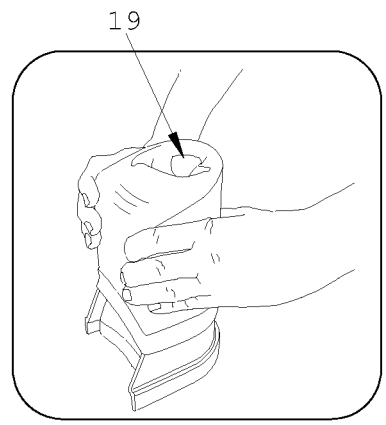

It will be appreciated that the drawings have been provided for the purposes of illustrating preferred embodiments of the present invention and that the invention should not be considered to be limited solely to the features as shown in the drawings.

Referring initially to FIG. 1, there is illustrated a compression stocking applicator 10. Applicator 10, in the particular embodiment, is made of smooth polyvinyl chloride and has a length of between 15-30 cm. Applicator 10 is somewhat U-shaped and comprises a pair of opposed sidewalls 11, 12 and an interconnecting wall 13. In the embodiment, the applicator 10 is a unitary structure.

The design of applicator 10 is such that the interconnecting wall 13 is smooth and curved. The sidewalls 11, 12 are substantially parallel to each other.

Applicator 10 has an "upper" end 14 and a "lower" end 15. Lower end 15 is square cut such that the applicator can stand in an upright position as illustrated in FIG. 1. Upper end 14 is cut on an angle and downwardly towards the sidewalls and then rounded as it meets the sidewalls. All the edges are rounded and smooth to prevent the stocking from being damaged when fitting the stocking to the applicator. It also gives a very smooth finish when the stocking is in place on the applicator (see FIG. 5).

Figure 14:
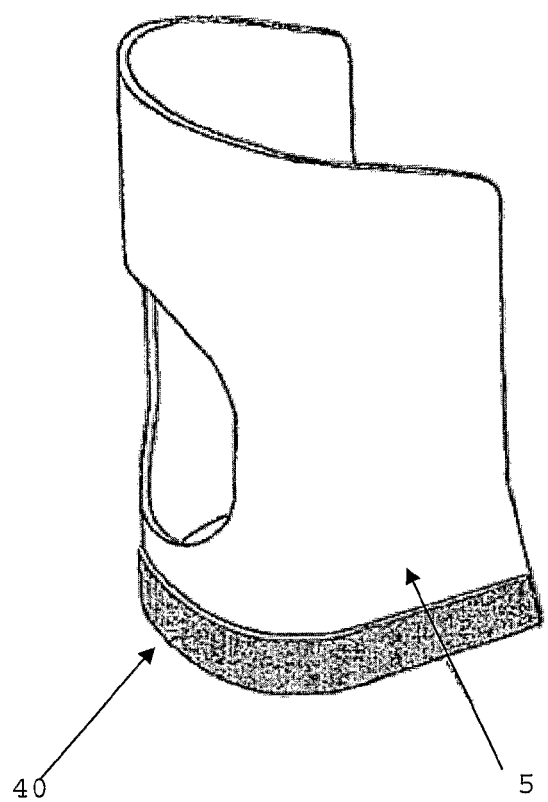
FIG. 14. Illustrates a variation having a raised surface.

If desired, the lower end 15 can be provided with a thickened or raised surface 40 of about 1 cm or so in height and extending about the lower end. This raised surface can provide a stocking stop and improve grip [see FIG. 14].

The interconnecting wall 13 contains a heel hole 16 which is substantially oval and is sized to allow a person's heel to at least partially project through the opening or engage with the opening. Of course, the hole could also be used to locate a person's elbow if the applicator is used on an arm.

In use, a medical stocking is initially fitted in a particular manner to applicator 10 and is then applied to a person's limb.

FIGS. 2-5 illustrate progressively how the stocking is fitted to applicator 10. This can be called the "loading procedure". The loading procedure is very user-friendly. For instance, applicator 10 can initially be placed on any flat surface (e.g. a table, a bed, a bench, or even your lap). The stocking 18 is then placed inside the applicator and the upper open end of the stocking is stretched over upper end 14 of applicator 10, this being illustrated in FIG. 2. Care should be taken that the heel 19 of the stocking 18 (heel 19 is clearly illustrated in FIG. 5 and also in FIG. 4) is in line with the heel hole 16 of applicator 10. This is not difficult to do. The stocking can then be progressively pushed down over the outside of applicator 10 (this being illustrated in FIGS. 3-5) until such time as the heel 19 of stocking 18 is adjacent the upper end 14 of the applicator, this being the position illustrated in FIG. 5.

Because of the smoothness of the outside wall of the applicator, the stocking will slide smoothly and easily down the outside of the applicator with very little effort.

Figure 5:
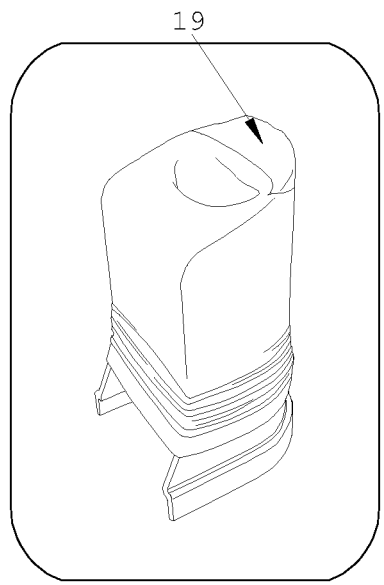
FIG. 5. Illustrates a stocking fitted to the applicator.
Figure 6:
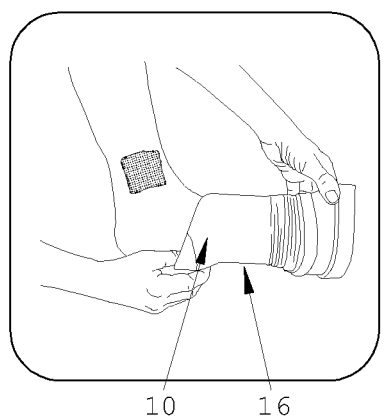
FIGS. 6-11. Illustrate progressively how the applicator applies to stocking over the person's lower limb.

In the position illustrated in FIG. 5, the stocking has now been "loaded" on the applicator and is ready for use.

FIG. 6-11 illustrate progressively how the loaded applicator can be used to apply a compression stocking over the lower limb of the person.

Figure 12:
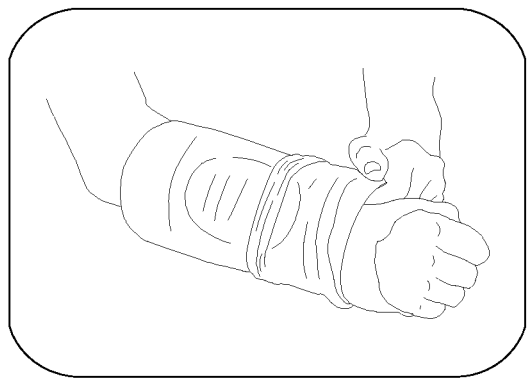
FIGS. 12-13. Illustrate how the same applicator can be used to apply a compression tubular bandage to a person's arm.
Figure 13:
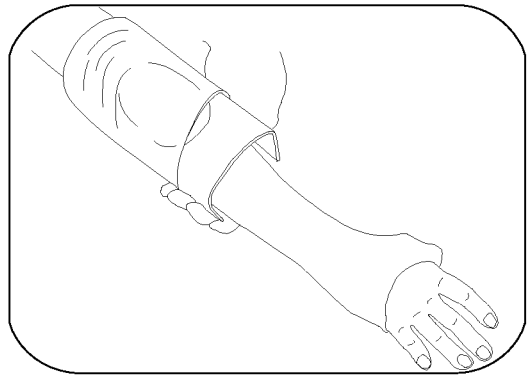

FIGS. 12-13 illustrate how the loaded applicator can be used to apply a compression stocking over persons arm.

Referring initially to FIG. 6-11, the loaded applicator is lightweight and easy to hold. A person will hold the heel part of 19 of the stocking 18 and places applicator 10 over the person's toes. By holding the heel part of the stocking, the person's foot can press through the centre of the stocking and the person's heel will be aligned with the heel portion in the stocking. This is the position illustrated in FIG. 6.

Figure 7:
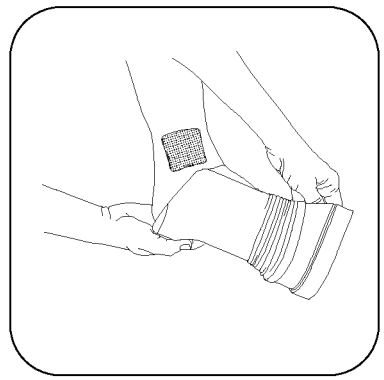

Referring now to FIG. 7, the applicator has been pushed towards the person's heel and at this stage, the stocking spools of the applicator with an even flow.

Figure 8:
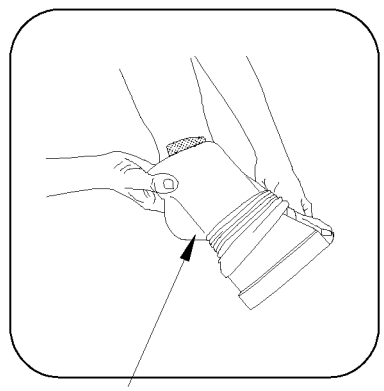

Referring now to FIG. 8, the applicator has been pushed further up the person's limb and the person's heel has now engaged in the heel hole 16 of the applicator. The applicator 10 can now change direction without restriction. This makes fitting of the stocking very smooth as the applicator is steering itself. The applicator is simply moved further up the person's leg and will complete the turn around the ankle and the stocking will continue to spool off the applicator.

Figure 9:
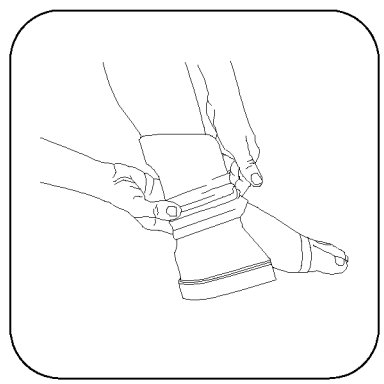

Referring now to FIG. 9, the person's heel has now moved past and out of heel hole 16 and the applicator is being pulled up the person's calf area with the stocking spooling off the applicator.

Figure 10:

Referring now to FIG. 10, the applicator has been pushed even further along the person's leg and the person's foot is now free from the applicator.

Figure 11:
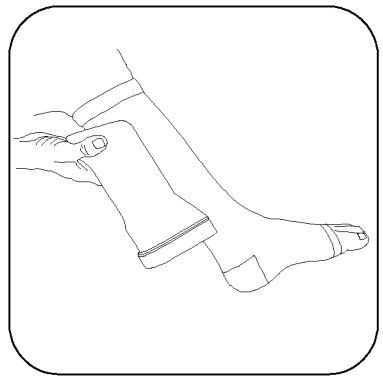

Referring now to FIG. 11, once all the stocking has been spooled off the applicator, the applicator 10 can be simply pulled away from the person's leg without needing to push the applicator back over the person's foot to remove the applicator.

FIGS. 12-13 illustrate how the same applicator can be used to attach a compression tubular bandage to a person's arm. Because of the compact design of the applicator, it has no problems in applying a stocking to an arm. The fitting is straight and smooth and is the less traumatic process for the patient.

Figure 15:
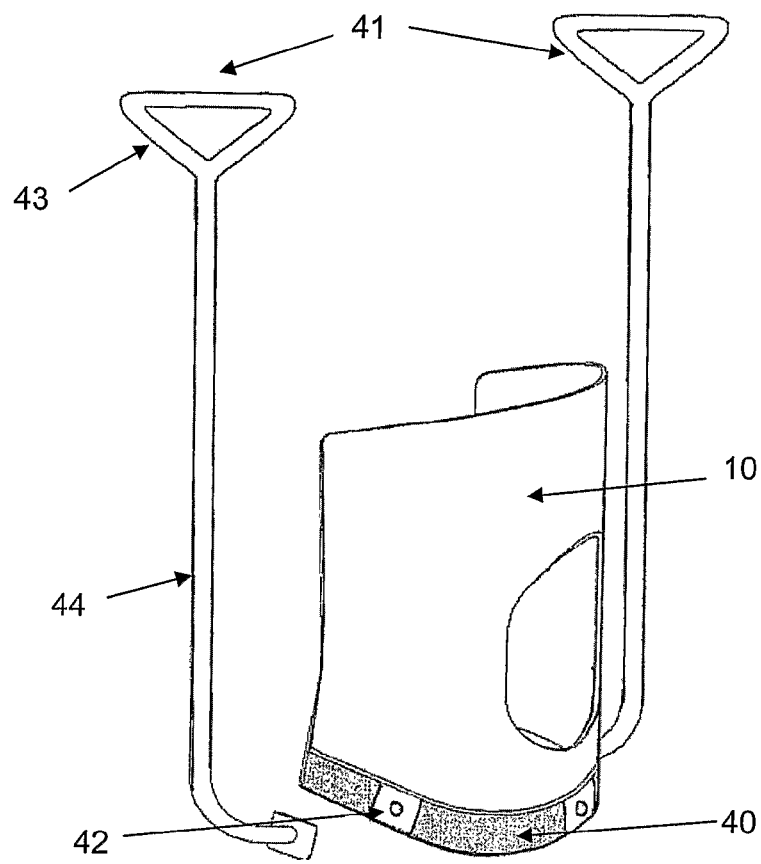
FIGS. 15-18. Illustrate handles which can be attached to the applicator.

FIG. 15 illustrates an applicator 10 according to one embodiment of the present invention in which the applicator 10 comprises a pair of removable handles 41 to assist in use of the applicator 10. The removable handles 41 are adapted to slot into holes 42 located on the thickened or raised surface 40 at the base of the applicator 10. The handles 41 of this embodiment of the invention comprise a grip portion 43 and a rigid elongate member 44 interconnecting the grip portion 43 and the applicator 10.

Figure 16:
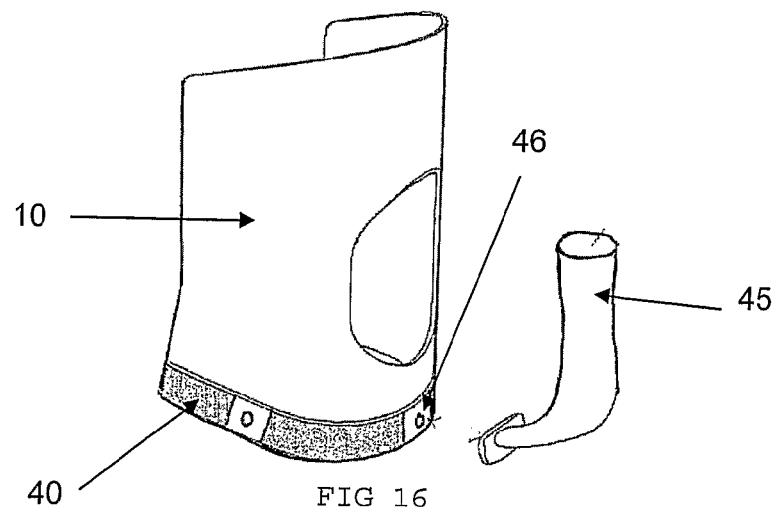

In FIG. 16, an alternative embodiment of the invention is shown in which the applicator 10 is provided with a single rigid handle 45 which slots into a hole 46 on the thickened or raised surface 40 at the base of the applicator 10.

Figure 17:
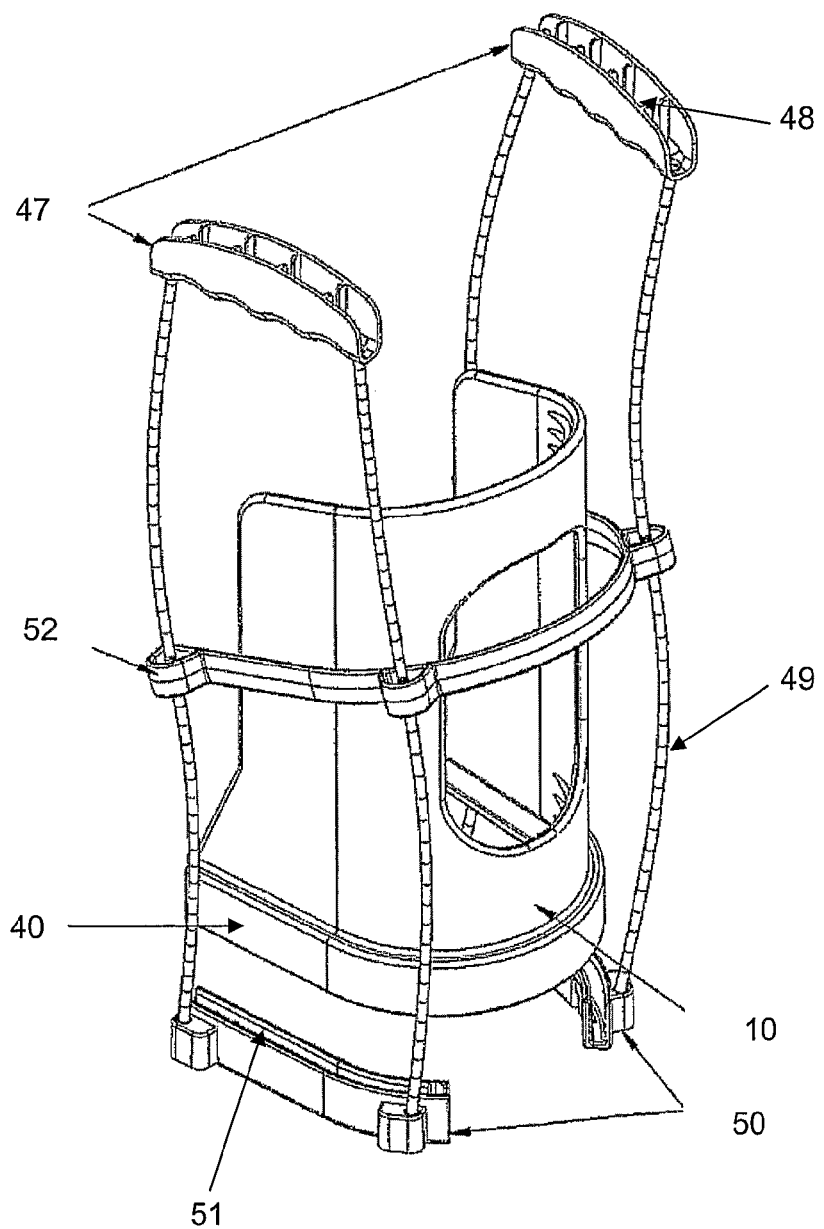
Figure 18:
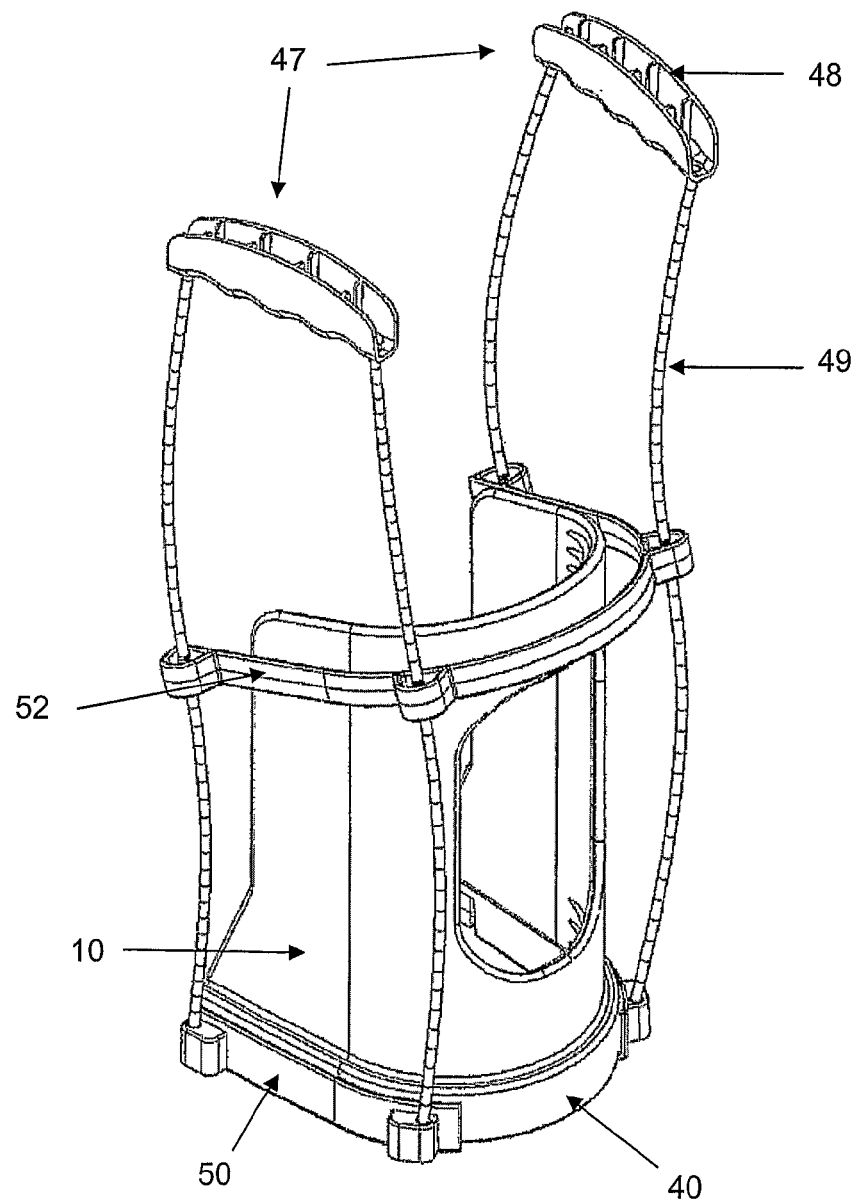

Turning now to FIGS. 17 and 18 there is shown an applicator 10 according to yet another embodiment of the present invention. The applicator 10 comprises a pair of handles 47 comprising a moulded grip portion 48 and a flexible rope 49 interconnecting the grip portion 48 and the a pair of clips 50. While the flexible rope 49 in this embodiment is constructed from nylon, any suitable material may be used in this application.

The clips 50 are provided with a channel 51 adapted to receive an edge of the base portion 40 of the applicator 10. The edge of the base portion slots into and is retained within the channel 51 when the applicator 10 is in use (see FIG. 18).

The applicator 10 illustrated in FIGS. 17 and 18 may further comprise an intermediate band 52 which acts as a guide for the flexible rope 49 and allows the use greater control when using the applicator 10. In the embodiment of the invention illustrated in FIGS. 17 and 18 the intermediate band 52 does not attach to the applicator 10, although in some other embodiments of the invention the intermediate band 52 may suitably be attached to the applicator 10 using any suitable method.

Figure 19:
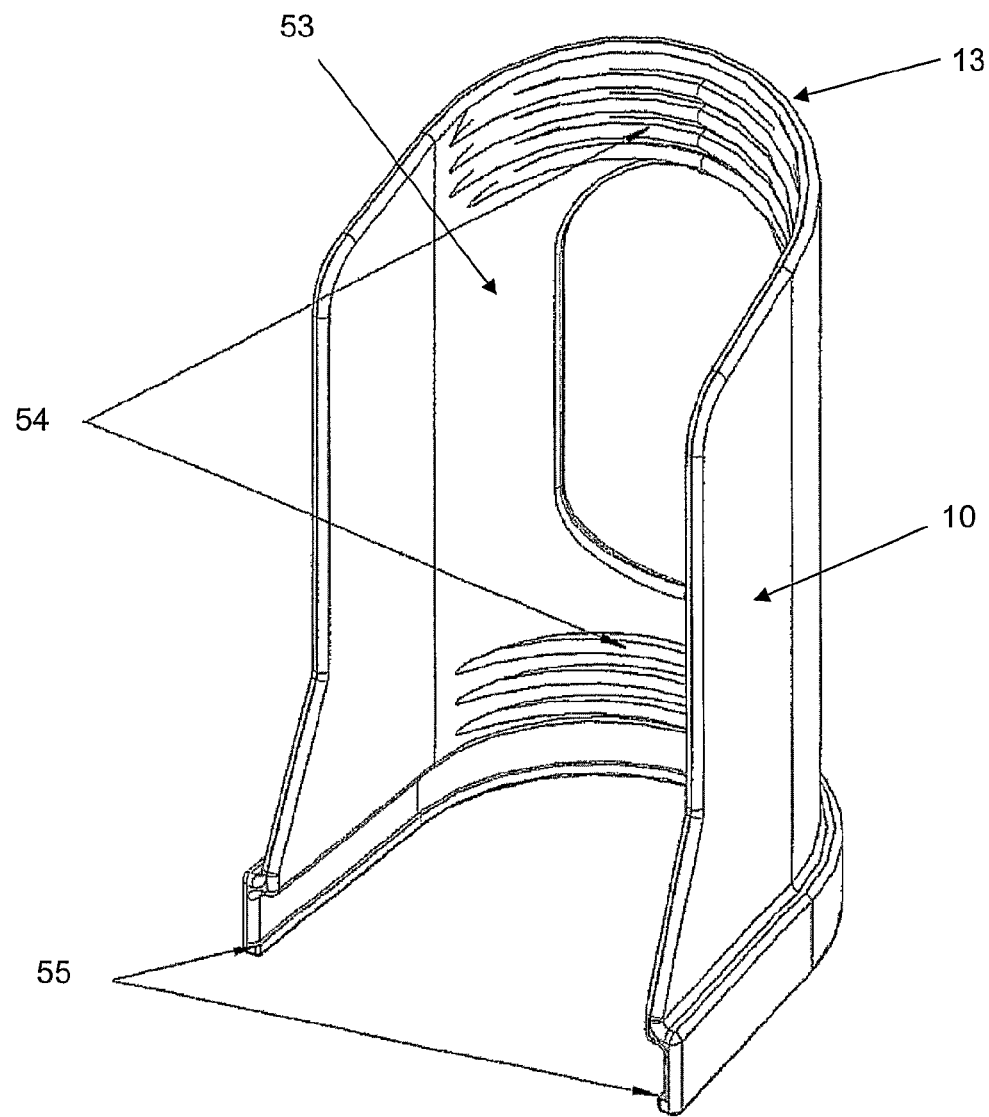
FIG. 19. Illustrates a perspective view of the inner surface of the applicator according to an embodiment of the present invention.

In FIG. 19 there is illustrated a rear view of an applicator 10 according to an embodiment of the present invention. The inner surface 53 of the interconnecting wall 13 of the applicator 10 comprises a plurality of raised portions in the form of ribs 54. The presence of these ribs 54 allows the interconnecting wall 13 to be of a reduced thickness while still retaining sufficient rigidity for the application of a high compression stocking or bandage (not shown).

The applicator 10 illustrated in FIG. 19 further comprises a lip 55 at the base of the applicator 10 shaped so as to slot into and be retained in the channel (not shown) of a clip (not shown) forming a part of one or more handles (not shown).

Figure 20:
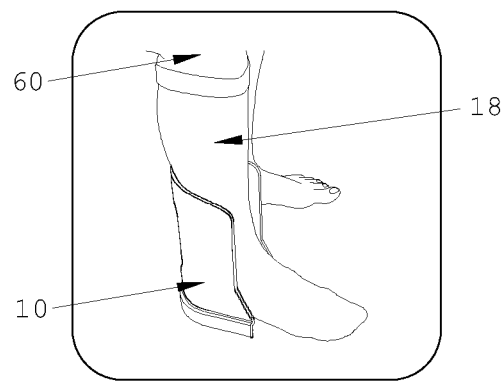
FIGS. 20-26. Illustrate progressively how to remove a stocking from a person's lower limb using the applicator according to an embodiment of the present invention.
Figure 21:
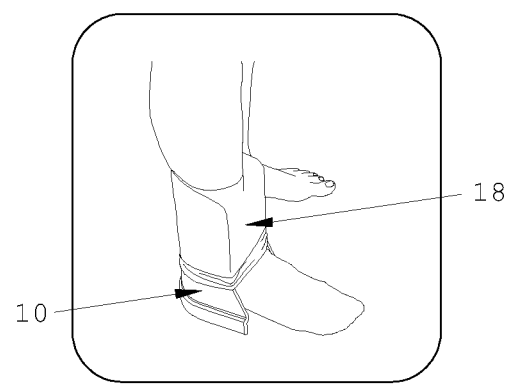
Figure 22:
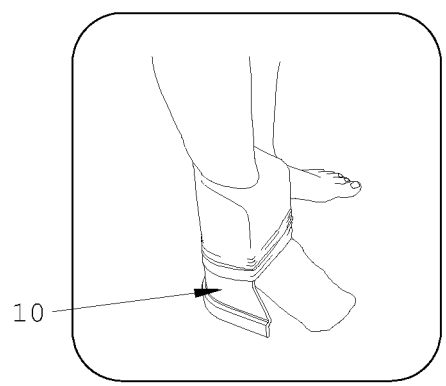
Figure 23:
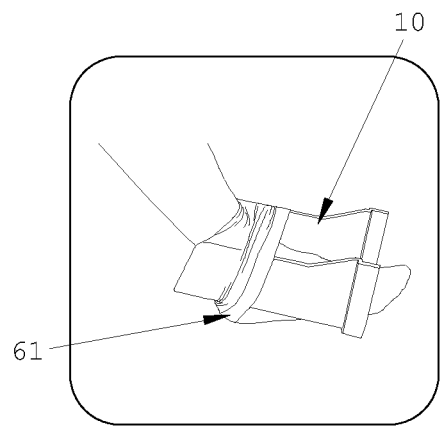
Figure 24:
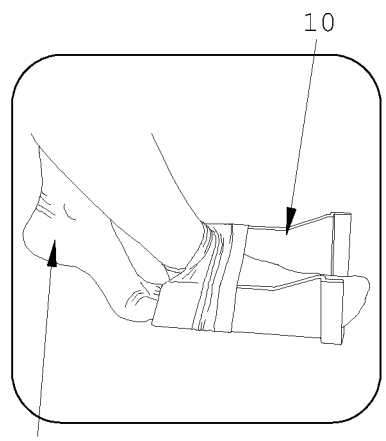
Figure 25:
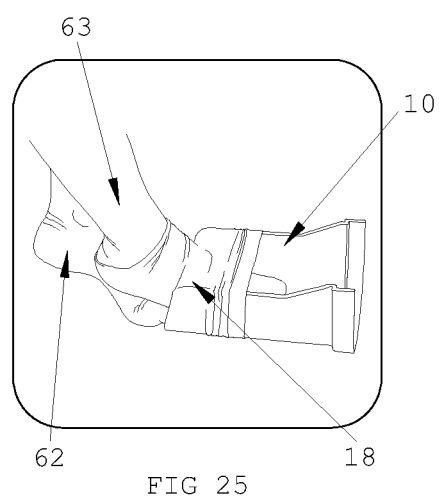
Figure 26:
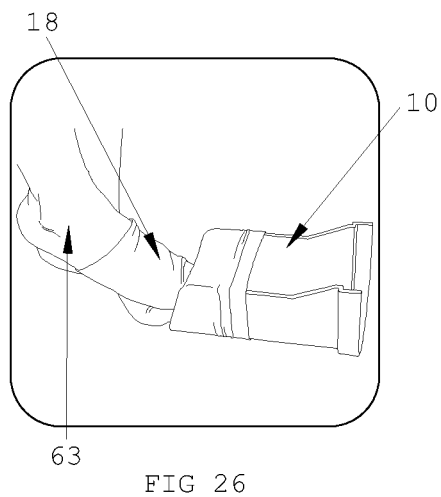

Turning now to FIGS. 20-26 there is illustrated progressively a method for removing a stocking 18 from a person's lower limb using the applicator 10 of the present invention. Firstly, as shown in FIG. 20, the applicator 10 is placed in an upright position against the back of the user's leg 60. The top of the stocking 18 may then be rolled down over the upper end of the applicator 10, as shown in FIG. 21. In FIG. 22 the person is shown lifting their heel off the ground in order to correctly position the applicator 10 for the remaining steps. In FIG. 23, the applicator 10 has been positioned such that the user's heel 61 is positioned in the heel opening (not shown) on the applicator 10. In FIG. 24, the applicator 10 is now placed in a horizontal position and is pushed forward using the user's other foot 62. In FIG. 24, the user continues to push the applicator 10 forward using their foot 62. As the user pushes the applicator 10 forward the stocking 18 begins to roll forward over the foot 63 to which it has been applied. In FIG. 26, the applicator 10 has been pushed so far forward that the stocking 18 may simply be rolled off the affected foot 63, or the person may pull their foot 63 backwards and clear of the stocking 18.

The applicator can apply and remove stockings/pressure bandages et cetera to and from both upper and lower limbs. There are many benefits of the applicator including that it is easy to operate, quick to operate, is user-friendly, can be used to upper and lower limbs, has smooth edges to make it safe to use, is less traumatic for the patient and the wound, does not damage the expensive stocking, is a compact single piece design, is lightweight compared to many other applicators in the marketplace, can cover a large range of compression stockings including open toe stockings, closed toe stockings, full leg stockings, light weight "Ted" stockings, and the like. The applicator is robust, is easy to clean, easy to store or pack away in a suitcase, and can be made relatively cheaply and economically.

Throughout the specification and the claims (if present), unless the context requires otherwise, the term "comprise", or variations such as "comprises" or "comprising", will be understood to apply the inclusion of the stated integer or group of integers but not the exclusion of any other integer or group of integers.

Throughout the specification and claims (if present), unless the context requires otherwise, the term "substantially" or "about" will be understood to not be limited to the value for the range qualified by the terms.

It should be appreciated that various other changes and modifications can be made to any embodiment described without departing from the spirit and scope of the invention.

The invention claimed is:

1. A stocking applicator comprising
an elongate member which comprises a pair of opposed sidewalls and an interconnecting wall providing a substantially U-shaped cross-section the length of the elongated member and is open at each end, the elongate member having a heel opening between the ends of the elongate member, said heel opening extending entirely through the interconnecting wall of the elongate member, the heel opening being positioned in the interconnecting member and between each of the pair of opposed sidewalls, wherein the heel opening is located substantially central the interconnecting portion and is adapted to allow a person's heel to pass through during application of a stocking.

2. The applicator as claimed in claim 1, including a raised surface provided at least partially about the opposed sidewalls and the interconnecting member of at least one end of the applicator, the raised surface able to function as a stocking stop and/or a grip enhancing surface.

3. The applicator of claim 1, wherein the stocking comprises a compression stocking or a tubular bandage.

4. The applicator of claim 1, having a length of between 10-50 cm.

5. The applicator of claim 1 comprising a unitary structure.

6. The applicator of claim 1 made of smooth material.

7. The applicator of claim 1 or 2, wherein one end of the applicator is formed substantially flat and this end is the lower end of the applicator in use.

8. The applicator as claimed in claim 7, wherein the opposite end of the applicator from the lower end is angled downwardly.

9. The applicator of claim 1, wherein the sidewalls are substantially parallel relative to each other and the interconnecting wall is curved.

10. The applicator of claim 1, wherein the heel opening is oval.

11. The applicator of claim 1, wherein the heel opening has a length of between 20-100 mm and a width of between 20-60 mm.

12. The applicator of claim 1, wherein an inner surface of the elongate member comprises one or more raised portions.

13. The applicator as of claim 1, wherein the applicator further comprises at least one handle.

14. The combination of an applicator of claim 1 together with a stocking which has been loaded onto the applicator.

15. Use of the applicator of claim 1 to apply a stocking to a person's limb.

16. The applicator of claim 1, wherein the heel opening is covered by a removable cover.

17. A stocking applicator comprising an elongate member which comprises a pair of opposed sidewalls and an interconnecting wall wherein the opposed sidewalls and interconnecting wall is substantially U-shaped in cross-section along the length of the elongated member and is open at each end, the elongate member having an opening in the interconnecting wall which is adapted to allow part of a person's limb to pass through the opening during application of a stocking over the limb, wherein the opening is 20-100 mm in diameter or length and 20-100 mm in width, wherein said opening extends entirely through the interconnecting wall of the elongate member.

18. A method of applying a stocking to a person's lower limb the method comprising providing an applicator which comprises a substantially U-shaped elongate body having a heel hole extending entirely through the elongate body intermediate the ends of the body, stretching an upper end of the stocking over one end of the applicator, pushing the stocking over the outside of the applicator towards the other end of the applicator until the heel portion of the stocking is adjacent the one end of the applicator, placing a person's heel in the heel portion of the stocking, pulling the applicator along the person's foot such that the person's heel enters into the heel hole of the applicator, and then moving the applicator up the person's calf area until such time as the stocking has been applied, and then removing the applicator from the person's leg.

19. A method of removing a stocking from a person's lower limb the method comprising placing an applicator which comprises a substantially U-shaped elongate body having a heel hole extending entirely through the elongate body intermediate the ends of the body against the limb, stretching an upper end of the stocking over one end of the applicator, pushing the stocking over the outside of the applicator towards the other end of the applicator, adjusting the position of the applicator to allow a person's heel to be placed in the heel hole, moving the applicator along the person's foot until such time as the stocking has been removed or the person is able to remove the foot from the stocking.

20. The stocking applicator of claim 1, wherein the heal opening is (a) 20-100 mm in diameter or length and 20-100 mm in width; or (b) sized such that a person's heel passes through the heel opening during the application of a stocking.

* * * * *